US012571402B2

(12) United States Patent
Toellner et al.

(10) Patent No.: US 12,571,402 B2
(45) Date of Patent: Mar. 10, 2026

(54) RADIALLY COMPRESSIBLE AND EXPANDABLE ROTOR FOR A PUMP HAVING AN IMPELLER BLADE

(71) Applicant: ECP ENTWICKLUNGSGESELLSCHAFT MBH, Aachen (DE)

(72) Inventors: Thomas Toellner, Aachen (DE); Mario Scheckel, Aachen (DE)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 71 days.

(21) Appl. No.: 18/402,909

(22) Filed: Jan. 3, 2024

(65) Prior Publication Data

US 2024/0328427 A1      Oct. 3, 2024

Related U.S. Application Data

(63) Continuation of application No. 17/139,170, filed on Dec. 31, 2020, now Pat. No. 11,913,467, which is a
(Continued)

(30) Foreign Application Priority Data

Jul. 15, 2010      (EP) ..................................... 10075302

(51) Int. Cl.
*F04D 29/18*      (2006.01)
*A61M 60/13*     (2021.01)
(Continued)

(52) U.S. Cl.
CPC ........... *F04D 29/181* (2013.01); *A61M 60/13* (2021.01); *A61M 60/174* (2021.01);
(Continued)

(58) Field of Classification Search
CPC ..... F04D 29/181; F04D 29/183; F04D 29/247
(Continued)

(56) References Cited

U.S. PATENT DOCUMENTS 3,510,229 A    5/1970   Smith
3,568,659 A    3/1971   Karnegis
(Continued)

FOREIGN PATENT DOCUMENTS

CA      1008330 A     4/1977
CA      2311977 A1    12/2000
(Continued)

OTHER PUBLICATIONS

Office Action in German Application No. 112011102353.7, dated Nov. 22, 2024 (10 pp.).
(Continued)

*Primary Examiner* — Kenneth J Hansen
(74) *Attorney, Agent, or Firm* — Botos Churchill IP Law LLP

(57)      ABSTRACT

The invention relates to a radially compressible and expandable rotor for a pump having at least one impeller blade, wherein the impeller blade has an impeller blade body whose material is elastically deformable as well as at least one stiffening strut which is at least partially embedded in the material of the impeller blade body. The struts are designed suitably in size, shape and arrangement and are integrated in suitable hollow spaces of the impeller blade body for stabilizing the impeller blade. Elements with tensile strength can additionally be provided.

18 Claims, 11 Drawing Sheets

Related U.S. Application Data continuation of application No. 16/859,064, filed on Apr. 27, 2020, now Pat. No. 10,920,596, which is a continuation of application No. 16/227,071, filed on Dec. 20, 2018, now Pat. No. 10,669,855, which is a continuation of application No. 15/429,277, filed on Feb. 10, 2017, now Pat. No. 10,196,899, which is a continuation of application No. 13/261,562, filed as application No. PCT/EP2011/003439 on Jul. 1, 2011, now Pat. No. 9,611,743.

(60) Provisional application No. 61/364,559, filed on Jul. 15, 2010.

(51) Int. Cl.

| | |
|---|---|
| *A61M 60/148* | (2021.01) |
| *A61M 60/174* | (2021.01) |
| *A61M 60/216* | (2021.01) |
| *A61M 60/414* | (2021.01) |
| *A61M 60/808* | (2021.01) |
| *F01D 5/14* | (2006.01) |

(52) U.S. Cl.
CPC ........ *A61M 60/216* (2021.01); *A61M 60/414* (2021.01); *A61M 60/808* (2021.01); *F01D 5/147* (2013.01); *A61M 60/148* (2021.01)

(58) Field of Classification Search
USPC ............... 416/2, 87, 132 R, 233, 240, 229 R
See application file for complete search history.

(56) References Cited

U.S. PATENT DOCUMENTS

| | | | |
|---|---|---|---|
| 3,802,551 | A | 4/1974 | Somers |
| 3,812,812 | A | 5/1974 | Hurwitz |
| 4,014,317 | A | 3/1977 | Bruno |
| 4,207,028 | A | 6/1980 | Ridder |
| 4,559,951 | A | 12/1985 | Dahl et al. |
| 4,563,181 | A | 1/1986 | Wijayarathna et al. |
| 4,679,558 | A | 7/1987 | Kensey et al. |
| 4,686,982 | A | 8/1987 | Nash |
| 4,747,821 | A | 5/1988 | Kensey et al. |
| 4,749,376 | A | 6/1988 | Kensey et al. |
| 4,753,221 | A | 6/1988 | Kensey et al. |
| 4,801,243 | A | 1/1989 | Norton |
| 4,817,613 | A | 4/1989 | Jaraczewski et al. |
| 4,919,647 | A | 4/1990 | Nash |
| 4,957,504 | A | 9/1990 | Chardack |
| 4,969,865 | A | 11/1990 | Hwang et al. |
| 4,995,857 | A | 2/1991 | Arnold |
| 5,011,469 | A | 4/1991 | Buckberg et al. |
| 5,040,944 | A | 8/1991 | Cook |
| 5,042,984 | A | 8/1991 | Kensey et al. |
| 5,052,404 | A | 10/1991 | Hodgson |
| 5,061,256 | A | 10/1991 | Wampler |
| 5,092,844 | A | 3/1992 | Schwartz et al. |
| 5,097,849 | A | 3/1992 | Kensey et al. |
| 5,108,411 | A | 4/1992 | Mckenzie |
| 5,112,292 | A | 5/1992 | Hwang et al. |
| 5,113,872 | A | 5/1992 | Jahrmarkt et al. |
| 5,117,838 | A | 6/1992 | Palmer et al. |
| 5,118,264 | A | 6/1992 | Smith |
| 5,145,333 | A | 9/1992 | Smith |
| 5,151,721 | A | 9/1992 | Allendorf et al. |
| 5,163,910 | A | 11/1992 | Schwartz et al. |
| 5,169,378 | A | 12/1992 | Figuera |
| 5,183,384 | A | 2/1993 | Trumbly |
| 5,191,888 | A | 3/1993 | Palmer et al. |
| 5,201,679 | A | 4/1993 | Velte et al. |
| 5,275,580 | A | 1/1994 | Yamazaki |
| 5,373,619 | A | 12/1994 | Fleischhacker et al. |
| 5,376,114 | A | 12/1994 | Jarvik |
| 5,501,574 | A | 3/1996 | Raible |
| 5,531,789 | A | 7/1996 | Yamazaki et al. |
| 5,701,911 | A | 12/1997 | Sasamine et al. |
| 5,749,855 | A | 5/1998 | Reitan |
| 5,755,784 | A | 5/1998 | Jarvik |
| 5,776,190 | A | 7/1998 | Jarvik |
| 5,813,405 | A | 9/1998 | Montano et al. |
| 5,820,571 | A | 10/1998 | Erades et al. |
| 5,851,174 | A | 12/1998 | Jarvik et al. |
| 5,877,566 | A | 3/1999 | Chen |
| 5,882,329 | A | 3/1999 | Patterson et al. |
| 5,888,241 | A | 3/1999 | Jarvik |
| 5,938,672 | A | 8/1999 | Nash |
| 6,030,397 | A | 2/2000 | Monetti et al. |
| 6,129,704 | A | 10/2000 | Forman et al. |
| 6,152,693 | A | 11/2000 | Olsen et al. |
| 6,168,624 | B1 | 1/2001 | Sudai |
| 6,254,359 | B1 | 7/2001 | Aber |
| 6,302,910 | B1 | 10/2001 | Yamazaki et al. |
| 6,308,632 | B1 | 10/2001 | Shaffer |
| 6,336,939 | B1 | 1/2002 | Yamazaki et al. |
| 6,346,120 | B1 | 2/2002 | Yamazaki et al. |
| 6,387,125 | B1 | 5/2002 | Yamazaki et al. |
| 6,503,224 | B1 | 1/2003 | Forman et al. |
| 6,506,025 | B1 | 1/2003 | Gharib |
| 6,508,787 | B2 | 1/2003 | Erbel et al. |
| 6,517,315 | B2 | 2/2003 | Belady |
| 6,527,521 | B2 | 3/2003 | Noda |
| 6,533,716 | B1 | 3/2003 | Schmitz-Rode et al. |
| 6,537,030 | B1 | 3/2003 | Garrison |
| 6,537,315 | B2 | 3/2003 | Yamazaki et al. |
| 6,592,612 | B1 | 7/2003 | Samson et al. |
| 6,652,548 | B2 | 11/2003 | Evans et al. |
| 6,719,791 | B1 | 4/2004 | Nuesser et al. |
| 6,790,171 | B1 | 9/2004 | Gruendeman et al. |
| 6,860,713 | B2 | 3/2005 | Hoover |
| 6,945,977 | B2 | 9/2005 | Demarais et al. |
| 6,981,942 | B2 | 1/2006 | Khaw et al. |
| 7,022,100 | B1 | 4/2006 | Aboul-hosn et al. |
| 7,027,875 | B2 | 4/2006 | Siess et al. |
| 7,054,156 | B2 | 5/2006 | Espinoza-ibarra et al. |
| 7,074,018 | B2 | 7/2006 | Chang |
| 7,179,273 | B1 | 2/2007 | Palmer et al. |
| 7,393,181 | B2 | 7/2008 | McBride et al. |
| 7,467,929 | B2 | 12/2008 | Nuesser et al. |
| 7,731,675 | B2 | 6/2010 | Aboul-hosn et al. |
| 7,841,976 | B2 | 11/2010 | Mcbride et al. |
| 7,927,068 | B2 | 4/2011 | Mcbride et al. |
| 7,934,909 | B2 | 5/2011 | Nuesser et al. |
| 8,079,948 | B2 | 12/2011 | Shifflette |
| 2002/0094273 | A1 | 7/2002 | Huang |
| 2002/0123661 | A1 | 9/2002 | Verkerke et al. |
| 2003/0135086 | A1 | 7/2003 | Khaw et al. |
| 2003/0231959 | A1 | 12/2003 | Snider |
| 2004/0044266 | A1 | 3/2004 | Siess et al. |
| 2004/0046466 | A1 | 3/2004 | Siess et al. |
| 2004/0093074 | A1 | 5/2004 | Hildebrand et al. |
| 2004/0215222 | A1 | 10/2004 | Krivoruchko |
| 2004/0215228 | A1 | 10/2004 | Simpson et al. |
| 2005/0101200 | A1 | 5/2005 | Townsend |
| 2006/0008349 | A1 | 1/2006 | Khaw |
| 2006/0062672 | A1 | 3/2006 | Mcbride et al. |
| 2006/0195004 | A1 | 8/2006 | Jarvik |
| 2007/0270875 | A1 | 11/2007 | Bacher et al. |
| 2008/0073983 | A1 | 3/2008 | Krajcir |
| 2008/0103591 | A1 | 5/2008 | Siess |
| 2008/0114339 | A1 | 5/2008 | McBride et al. |
| 2008/0132747 | A1 | 6/2008 | Shifflette |
| 2008/0132748 | A1 | 6/2008 | Shifflette |
| 2008/0262584 | A1 | 10/2008 | Bottomley et al. |
| 2008/0306327 | A1 | 12/2008 | Shifflette |
| 2009/0060743 | A1 | 3/2009 | Mcbride et al. |
| 2009/0093764 | A1* | 4/2009 | Pfeffer ................ A61M 60/896<br>604/151 |
| 2009/0093796 | A1 | 4/2009 | Pfeffer et al. |
| 2010/0041939 | A1 | 2/2010 | Siess |
| 2010/0268017 | A1 | 10/2010 | Siess |
| 2011/0071338 | A1 | 3/2011 | McBride et al. |
| 2011/0236210 | A1 | 9/2011 | McBride et al. |
| 2011/0238172 | A1 | 9/2011 | Akdis |

(56)                    References Cited

U.S. PATENT DOCUMENTS

| | | |
|---|---|---|
| 2011/0257462 A1 | 10/2011 | Rodefeld et al. |
| 2011/0275884 A1 | 11/2011 | Scheckel |
| 2012/0039711 A1 | 2/2012 | Roehn |
| 2012/0039713 A1 | 2/2012 | Shifflette |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1* | 11/2012 | Er ........................ A61M 60/205 |
| | | 416/223 R |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner et al. |
| 2013/0204362 A1 | 8/2013 | Toellner et al. |
| 2013/0237744 A1 | 9/2013 | Pfeffer et al. |
| 2014/0039465 A1 | 2/2014 | Schulz et al. |

FOREIGN PATENT DOCUMENTS

| | | | |
|---|---|---|---|
| CA | 2701809 A1 | 4/2009 | |
| CA | 2701810 A1 | 4/2009 | |
| DE | 2207296 A1 | 8/1972 | |
| DE | 2113986 A1 | 9/1972 | |
| DE | 2233293 A1 | 1/1973 | |
| DE | 2613696 A1 | 10/1977 | |
| DE | 4124299 A1 | 1/1992 | |
| DE | 69103295 T2 | 12/1994 | |
| DE | 19535781 A1 | 3/1997 | |
| DE | 19711935 A1 | 4/1998 | |
| DE | 29804046 U1 | 4/1998 | |
| DE | 69407869 T2 | 4/1998 | |
| DE | 69017784 T3 | 4/2000 | |
| DE | 69427390 T2 | 9/2001 | |
| DE | 10059714 C1 | 5/2002 | |
| DE | 10108810 A1 | 8/2002 | |
| DE | 10155011 A1 | 5/2003 | |
| DE | 69431204 T2 | 8/2003 | |
| DE | 10336902 B3 | 8/2004 | |
| DE | 102010011998 A1 | 9/2010 | |
| DE | 10336902 C5 | 4/2019 | |
| EP | 0364293 A2 | 4/1990 | |
| EP | 480102 A1 | 4/1992 | |
| EP | 560000 A2 | 9/1993 | |
| EP | 768091 A1 | 4/1997 | |
| EP | 0629412 B1 | 1/1998 | |
| EP | 0884064 A2 | 12/1998 | |
| EP | 1019117 A1 | 7/2000 | |
| EP | 1061968 A1 | 12/2000 | |
| EP | 1066851 A1 | 1/2001 | |
| EP | 0914171 B1 | 10/2001 | |
| EP | 1337288 A1 | 8/2003 | |
| EP | 0916359 B1 | 9/2004 | |
| EP | 0951302 B1 | 9/2004 | |
| EP | 1114648 B1 | 9/2005 | |

| | | |
|---|---|---|
| EP | 1651290 A1 | 5/2006 |
| EP | 2047872 A1 | 4/2009 |
| EP | 2194278 A1 | 6/2010 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 2497521 A1 | 9/2012 |
| EP | 2606919 A1 | 6/2013 |
| EP | 2606920 A1 | 6/2013 |
| EP | 2607712 A1 | 6/2013 |
| GB | 2239675 A | 7/1991 |
| GB | 2405677 A | 3/2005 |
| RU | 2229899 C2 | 6/2004 |
| WO | 9202263 A1 | 2/1992 |
| WO | 9302732 A1 | 2/1993 |
| WO | 9303786 A1 | 3/1993 |
| WO | 9314805 A1 | 8/1993 |
| WO | 9401148 A1 | 1/1994 |
| WO | 9405347 A1 | 3/1994 |
| WO | 9409835 A1 | 5/1994 |
| WO | 9618358 A1 | 6/1996 |
| WO | 9744071 A1 | 11/1997 |
| WO | 9853864 A1 | 12/1998 |
| WO | 9919017 A1 | 4/1999 |
| WO | 03103745 A2 | 12/2003 |
| WO | 2003103745 A2 | 12/2003 |
| WO | 2005002646 A1 | 1/2005 |
| WO | 2005016416 A1 | 2/2005 |
| WO | 2005021078 A1 | 3/2005 |
| WO | 2005030316 A1 | 4/2005 |
| WO | 2005032620 A1 | 4/2005 |
| WO | 2005081681 A2 | 9/2005 |
| WO | 2006020942 A1 | 2/2006 |
| WO | 2006034158 A2 | 3/2006 |
| WO | 2006051023 A1 | 5/2006 |
| WO | 2006133209 A1 | 12/2006 |
| WO | 2007003351 A1 | 1/2007 |
| WO | 2007103390 A2 | 9/2007 |
| WO | 2007103464 A2 | 9/2007 |
| WO | 2007112033 A2 | 10/2007 |
| WO | 2008017289 A2 | 2/2008 |
| WO | 2008034068 A2 | 3/2008 |
| WO | 2008054699 A2 | 5/2008 |
| WO | 2008106103 A2 | 9/2008 |
| WO | 2008116765 A2 | 10/2008 |
| WO | 2008124696 A1 | 10/2008 |
| WO | 2008137352 A1 | 11/2008 |
| WO | 2008137353 A1 | 11/2008 |
| WO | 2009015784 A1 | 2/2009 |
| WO | 2009029959 A2 | 3/2009 |
| WO | 2009073037 A1 | 6/2009 |
| WO | 2010133567 A1 | 11/2010 |
| WO | 2013034547 A1 | 3/2013 |
| WO | 2013092971 A1 | 6/2013 |
| WO | 2013093001 A2 | 6/2013 |
| WO | 2013093058 A1 | 6/2013 |

OTHER PUBLICATIONS

Office Action issued in Chinese Patent Application No. 201611144079.0 dated Nov. 23, 2020 (13 pages).

International Search Report and Written Opinion from International Application No. PCT/EP2011/003439 dated Oct. 19, 2011 (8 pp.).

Office Action issued in Chinese Patent Application No. 2021106275099 dated Sep. 26, 2023 (14 pp.).

* cited by examiner

RADIALLY COMPRESSIBLE AND EXPANDABLE ROTOR FOR A PUMP HAVING AN IMPELLER BLADE

CROSS-REFERENCE TO RELATED APPLICATIONS

This application is a continuation of U.S. patent application Ser. No. 17/139,170, filed Dec. 31, 2020, now U.S. Pat. No. 11,913,467, which application is a continuation of U.S. application Ser. No. 16/859,064, filed Apr. 27, 2020, now U.S. Pat. No. 10,920,596, which is a continuation of U.S. patent application Ser. No. 16/227,071, filed Dec. 20, 2018, now U.S. Pat. No. 10,669,855, which is a continuation of U.S. patent application Ser. No. 15/429,277, filed Feb. 10, 2017, now U.S. Pat. No. 10,196,899, which is a continuation of U.S. patent application Ser. No. 13/261,562, filed Mar. 15, 2013, now U.S. Pat. No. 9,611,743, which entered the national stage on Mar. 15, 2013, and which is a national phase entry under 35 U.S.C. § 371of International Application No. PCT/EP2011/003439, filed Jul. 1, 2011, published as WO/2012/007140, which claims the benefit of U.S. Provisional Patent Application No. 61/364,559, filed Jul. 15, 2010, and European Patent Application No. 10075302.9, filed Jul. 15, 2010, all of which are incorporated herein by reference in their entirety.

BACKGROUND OF THE INVENTION

The invention is in the field of mechanical engineering and mechanics and relates to rotors for pumps.

Rotor pumps can be used in a versatile manner and are very powerful with a corresponding design and speed of the rotor. The rotors can generally be designed as axially conveying or centrifugally conveying rotors and have corresponding impeller blades.

Such pumps are of particular interest when they are made very small in relationship with their conveying power in that they can be compressed for transport and expanded for operation. A specific application of such pumps in the medical field relates to invasive pumps which can be conveyed into the body of a patient in the radially compressed state and can be expanded there to achieve the desired conveying power.

Such pumps can be used, for example, as heart-assisting blood conveying pumps and can be conveyed through a blood vessel into a bodily cavity in order to be radially expanded there. Typically for this purpose, both the rotor and, where present, also a corresponding pump housing are radially compressible and expandable.

Such a pump is known, for example, from the U.S. Pat. No. 7,393,181 B2. With a rotor, a plurality of vanes are manufactured in one piece with a hub there and can be folded onto said hub in the transport state due to their material elasticity in order to compress the rotor radially. In operation, the vanes erect themselves so that the conveying power is increased accordingly. The material of the rotor there has to be selected carefully with respect to its elasticity properties and deformability properties in order, on the one hand, to be able to be pressed easily to the hub and, on the other hand, to be able to exert sufficient force on the liquid to be conveyed in operation.

A very similar pump is known from U.S. Patent Application Publication No. 2008/0114339 A1, where a corresponding rotor additionally cooperates with a housing which is likewise compressible and expandable. The housing is said to be expanded by the force effect of the erecting rotor vanes in the operation of the rotor.

Against the background of this prior art, it is the underlying object of the present invention to provide a rotor for a pump which can be radially compressed with as little exertion of force as possible and which, on the other hand, can be expanded just as easily in operation and has the required stability for the thrust effect in the expanded state.

BRIEF SUMMARY OF THE INVENTION

The object is achieved in accordance with the invention by the features of claim 1.

There is provided for this purpose in accordance with the invention a radially compressible and expandable rotor for a pump having at least one impeller blade, wherein the impeller blade has an impeller blade body whose material is elastically deformable as well as at least one stiffening strut which is at least partially embedded in the material of the impeller blade body.

The rotor in accordance with the invention preferably shows a support structure (=struts) which does not have any closed edge structure or edge curve. This means that, in the present invention, individual struts or blades are preferably provided which can be deformed largely independently of one another and thereby enable a good compression of the rotor, on the one hand, but also enable a sufficient stabilization/stiffness in pump operation, on the other hand. The impeller blade body has geometry-maintaining properties with respect to deformations in pump operation which are locally stiffened by stiffening struts.

In this respect, the surface of the impeller blade body is not pierced by the struts so that no interference in the fluid flow is caused. The impeller blade thickness (i.e. the total thickness of the impeller blade including any hollow spaces) preferably amounts to at least 80%, in particular 100%, advantageously more than the largest thickness of the struts adjacent thereto or connected thereto, measured in the direction of the thickness of the impeller blade, i.e. between the pressure side and the suction side. The vane wall thickness in the region in which the struts are positioned, including the region disposed between the struts in the direction transverse to the longitudinal direction of the struts, in particular viewed substantially perpendicular to the longitudinal direction of the struts, is advantageously substantially or completely constant.

The thickness of the struts can be designed variably, for example radially outwardly reducing with respect to the rotor axis, along its longitudinal direction. In this case, the thickness of the impeller blade can also reduce in this direction.

In addition, the thickness of the impeller blade can also increase or reduce outside the region reinforced by struts, for example at the lateral ends of the impeller blade.

An optimization of the flow along the impeller blade without any larger eddies and a minimized impeller blade surface is achieved by the largely constant thickness development of the impeller blade/blades.

The respective strut is thereby covered at all sides by the plastic material of the impeller blade and (unlike, for example, in film-covered metal structures) a homogeneous vane surface favorable for the flow produced. A considerably more shape-stable rotor which deflects under pressure in the flow field less and more uniformly and which thereby also behaves less sensitively toward production tolerances is also produced with respect to film-covered metal structures or similar rotors in which the thickness of the membrane between the struts rarely achieved 10%, in extreme cases a maximum of 50% of the strut thickness.

The different mechanical demands on the rotor or on the impeller blade can be distributed over different materials or construction elements by this construction. The struts can be built and positioned so that they do not impede the compression of the impeller blade from the first state into the second state, but that they, on the other hand, stabilize the rotor sufficiently in the third, expanded state. The struts thus take over the tensions, whereas the material of the impeller blade body has the required stretchability. In this respect, the total mass and the total volume of the rotor or of the impeller blade can also be minimized by the use of a composite material. This results in a small diameter in the second, compressed state.

The struts typically comprise a stiffer material than the impeller blade body, for example a stiff plastic or a metal alloy or a metal.

The construction is designed so that the rotor adopts a first state without an external force effect from which it can be moved, on the one hand, by a radial compression into a second, compressible state for purposes of transport, whereas it can be moved equally from the first state in operation by erecting the impeller blade/blades into a third, expanded state.

Since the first state of the rotor is already partially compressed with respect to the operating state, the radial forces required for the final compression should be minimized as much as possible. The impeller blade/blades moreover adopt(s) a preferred position in the first state which provides for an erection of the impeller blades under the effect of the fluid counter-pressure as well as for the fact that their position is optimized in the second, compressed state.

The rotor can advantageously be designed hubless and the struts can extend in the radial direction with respect to the axis of rotation from a first axial spacing to a second axial spacing. This means that the struts do not have to extend radially inwardly up to the axis of rotation, but rather extend at a finite spacing starting therefrom radially outwardly in the impeller blade. They can extend radially outwardly up to the end of the impeller blade or end at a second axial spacing before the end of the impeller blade. The impeller blade itself can be divided and leave the region close to the axis of rotation free or a single, throughgoing vane can extend beyond the central region, for example, as a single, spiral vane.

On the other hand, a hub can be provided to which the impeller blade is connected and with respect to which the impeller blade is pivotable. In this case, the introduction of the drive forces into the impeller blade through the hub is possible in a simplified manner, whereas with a hubless rotor the driving force has to be introduced into the impeller blades at the end face.

At least one strut, in particular also a plurality of struts or all struts, can advantageously extend radially up to and into the hub. The struts can, for example, be plugged into the hub body as individual bodies or as a connected structure or can be pulled into a groove of the hub body to form the support structure of the impeller blade. Such a groove-like recess of the hub body typically extends helically along its jacket surface. In cross-section, the groove can, for example, be formed in the manner of a dovetail to hold the struts reliably.

However, provision can also advantageously be made that at least one strut, in particular a plurality of struts or all struts, extend radially from a first axial spacing outside the hub up to a second axial spacing. In this case, the folding of the impeller blade onto the hub can be facilitated, for example. A folding in by a correspondingly optimized design is, however, also easily possible with struts which extend into the hub body or run through the hub in one piece.

The struts can all be connected to one another or can be connected to one another in groups, with them advantageously being able to be connected to one another within the half of their radial extent close to the axis of rotation, viewed in the expanded state of the rotor. They can in particular also be connected to one another at their ends close to the axis of rotation, advantageously also exclusively there. Provision can also be made that the struts are each connected to one another pairwise at their ends remote from the axis of rotation and thus form loops, with the loops each being connected on one another in the region close to the axis. A good stiffening of the impeller blade in the direction perpendicular to the thrust load hereby results and a good deformability within the plane of the impeller blade so that, in operation, a good stabilization is enabled by the struts, but the struts can have a corresponding movability among one another in the axially remote region of the impeller blade for the compression. The struts can be formed as strand-like bodies, for example in the form of a wire, but also as flat parts of a sheet metal-like body. In an advantageous embodiment, they can, for example, be punched out of a full metal sheet or can be cut out by corresponding cutting techniques, for example, laser cutting, etching or erosion.

The struts are advantageously insert molded or cast around with the material of the impeller blade body or are wetted by it in the liquid state, with a subsequent hardening accordingly being able to be provided.

Provision can furthermore advantageously be made that the struts are arranged in recesses of the impeller blade body which are larger in the longitudinal direction and/or transverse direction of the respective strut than the outer dimensions of the strut(s).

Since the recesses in the impeller blade body are larger in at least one direction of extent than the dimensions of the respective strut, the strut can be disposed in different positions in the respective recess in the different states of the rotor. Different degrees of stiffness of the impeller blade can thus be realized in the different states so that, on the one hand, the impeller blade can exert a strong stiffening effect in the extended state of the impeller blade in a first position and, on the other hand, can surroundingly support the same strut on the compression of the rotor within its recess such that it only insignificantly impairs the compression.

Provision can also advantageously be made that at least one strut adheres to the material of the impeller blade body on its surface facing the pressure side of the impeller blade and/or on its surface facing the suction side. For example, when the strut is adhesively connected to the material of the impeller blade body only on the surface facing the suction side and the material of the impeller blade is not compressible, a high stiffness can be achieved in the extended state. Depending on the requirements of the construction, the respective strut can only be adhesively connected to the impeller blade body on surface facing the suction side or on the pressure side or the strut can adhere to the impeller blade body all round at all of its surfaces.

In a further embodiment, the adhesion between the impeller blade body and the strut(s) can be different. The rotor can, for example, be designed so that the impeller blade body is fixedly connected to the struts in the region of the hub, whereas it does not adhere in the region of the struts remote from the hub and can thus slide with respect to the struts on compression. This can be done e.g. by the local use of adhesive means or separating means or by a different surface design (i.e. roughness, shape matching). Any desired embodiments are possible here: e.g. the rotor can also be designed so that the impeller blade body slides with respect to the struts in the region of the hub and is fixedly connected to the struts in the region remote from the hub. It can also vary over the length of the rotor.

The strut(s) can at least partially comprise a super elastic material, in particular a super elastic polymer, or a memory alloy, in particular nitinol. In this respect, a super elastic material is understood as a material which at least withstands an elastic stretching by 2% and afterward returns in a force-free manner substantially into its starting position.

The material of the impeller blade body can also comprise a super elastic material, for example to minimize or prevent crack formation, particularly at the radially outer tips of the impeller blade and in the region of the impeller blade root at the hub.

The strut or struts could be arranged at least partially obliquely with respect to the axial direction of the axis of rotation so that they adopt an angle of less than 90° toward the axial direction. In this case, on the compression into the second state, the respective impeller blade cannot only be placed onto the hub in the peripheral direction but can also be partially folded in the direction of the axis of rotation.

This has the advantage that a compression movement takes place partially in the plane of the impeller blade since usually no stiffening of the impeller blade by the struts is necessary in this direction. The struts can therefore permit a limited movement in the impeller blade plane despite the good stiffening properties.

A further advantageous embodiment of the invention provides that the impeller blade has at least one element with tensile strength in the form of a band or of a film which is connected at at least one radially outer fastening point and at at least one radially inner fastening point to a strut and/or to the impeller blade body.

Such an element with tensile strength stabilizes the impeller blade in the third, extended state without noticeably preventing or making more difficult the compression into the first state. The corresponding element with tensile strength can extend either directly in the radial direction or also obliquely to the axis of rotation, in particular parallel or substantially parallel to the struts.

Provision can moreover advantageously be made that the rotor has at least at the pressure side of the impeller blade at least one element with tensile strength in the form of a band or of a film which is fastened to a strut and/or to the impeller body at a radial spacing from the axis of rotation, on the one hand, and is fastened to a hub, on the other hand. The element with tensile strength can thus also be fastened to the hub at the foot of the respective impeller blade spaced apart from its root. The element with tensile strength can also continue the contour of the impeller blade as a film.

The element with tensile strength can moreover advantageously contain glass fibers, polycarbonate fibers or other reinforcing fibers. They have a very high tensile strength and resistance to stretching with a low weight and volume.

Provision can moreover be made that the element with tensile strength at least partially adheres to the surface of a strut or of the impeller blade body. In this case, the element with tensile strength becomes an additional layer of the strut or of the impeller blade body and a composite body is created locally having the desired mechanical properties such as flexural strength in one direction of load and, optionally, flexibility in the opposite direction.

The element with tensile strength can, for example, efficiently be adhered, sprayed on molded or printed onto the strut or onto the impeller blade.

The pressing on can take place using all common techniques which are also used for applying optically recognizable symbols on printable surfaces. It is moreover possible to apply the element with tensile strength by welding or firing in by means of a laser.

The element with tensile strength can extend, for example, winding in the manner of a meander in the first state of the rotor. The corresponding windings should be characterized so that the element with tensile strength can extend in the course of the stretching of the impeller blade on the shaping into the third state and can thus effectively bound the further movement of the impeller blade.

It is, for example, also conceivable to provide a pattern of elements with tensile strength spreading out in ray shape on an impeller blade, said elements starting, for example, from a common base at the root of the impeller blade and moving away from one another radially toward the outside of the impeller blade.

The curve of the force lines within the impeller blade on adopting the desired geometrical three-dimensional shape in the third state can also be calculated by corresponding calculations and can be mapped by corresponding positioning of the elements with tensile strength.

A further advantageous embodiment of the invention provides that the impeller blade is pivotably supported in a recess of a hollow cylindrical hub at the jacket side. It is the point of this arrangement to limit the material deformation at the root of the impeller blade as much as possible on the deformation between the first and third states of the impeller blade to avoid crack formation and other fatigue phenomena of the material. For this purpose, the stretching forces acting in the region of the root of the impeller blade are minimized. Corresponding holding forces on the impeller blade are not produced by connecting the impeller blade to the hub, but by other structures. The impeller blade can be held, for example, by a film hinge or by weakening the material of the hub in the region of the hub.

The invention can moreover advantageously provide that an inner end of the impeller blade projects through the opening into the cylindrical hollow space of the hub. The impeller blade is then supported in the wall of the hub body in the manner of a two-arm lever.

Provision can then also be made that the inner end cooperates with a fixed abutment in the hollow space of the hub in the third state.

The hollow space within the hub can be designed by integration of a fixed abutment such that a movement of the inner end of the impeller blade is limited there after reaching the third state.

On the compression of the rotor and of the impeller blade, a movement takes place in the opposite direction so that the inner end of the impeller blade also moves away from the fixed abutment in the interior of the hub and moves as freely as possible in order not to impede the movement of the impeller blade.

Provision can also be made that at least one strut of the impeller blade projects into the cylindrical hollow space of the hub.

The strut or struts of the impeller blade can project into the interior of the hub within the impeller blade body or also separately therefrom. In the latter case, the impeller blade body can end at the wall of the hub and only the struts can project into the interior of the hollow cylindrical hub. The individual struts can then, for example, each have an abutment body at their ends projecting into the hollow space of the hub and said abutment body cooperating with a fixed abutment of the hub in the third state.

A corresponding abutment body at the ends of the struts can in each case be formed as a sheet metal part which is disposed perpendicular to the axis of rotation and which can also be contiguous in one piece with the respective strut. The respective strut and abutment body can thus be manufactured simply in continuous form, e.g. by punching out of a flat body such as a metal sheet.

The abutment can, however, also be formed by the strut of the oppositely disposed impeller blade.

The abutment within the hub can advantageously be formed in one piece on the manufacture of the hub and integrated with it.

An embodiment of the (preferably super elastic) struts is preferably such that the permitted elastic stretching is not exceeded (not even locally) at any point of the struts either on the compression or in the operating state. This has to be taken into account in the geometrical design of the struts, for example that they are of a meandering kind.

A further development of the invention provides that the at least one impeller blade has a flow pressure side and a flow suction side and at least one stiffening strut is designed so that the stiffening strut has a mechanical abutment on reaching the third, expanded state. This mechanical abutment can be designed in different manner. It is, for example, possible that the stiffening strut is weakened on the flow suction side. On a radial compression of the rotor (into the supported introduction state), the compression is hereby facilitated, whereas a self-stiffening effect occurs on the movement against the fluid pressure (that is in the conveying operation).

This can, for example, be ensured in that the slits applied transversely to the longitudinal web direction represent the weakening. In the above-named third state in which the abutment is present, the inner walls of these slits can either be directly pressed onto one another or, if plastic or other embedding material is present here, a corresponding compression can be present so that an abutment situation results here. It is only important that the rotor unfolds in the fluid such that a mechanical "abutment" is present here. "Abutment" is here understood as a disproportionate exertion of force which is opposed to the fluid pressure; a defined position is hereby possible in the third state (operating state).

A further advantageous further development provides that the stiffening strut has a stiffening curvature, preferably in the region radially close to the hub. This can be a "knee" which ensures additional stability in the one direction here with a simultaneously improved deformability in the opposite direction. This can be optimized within the framework of the ability of the skilled person, for example such that the stretching of the components amounts to less than 8% overall. It can thus be prevented with a material, for example with a shape memory material, from which the stiffening strut is formed that the plastic region of the deformation is entered here.

A further advantageous further development provides that the stiffening strut is attached in the region of the rotor front edge, in the region of the rotor rear edge and/or at another point of the rotor. This means that a plurality of blades do not have to be applied distributed axially over the length of the rotor here, but that stiffening struts at spots are also sufficient here, in particular at points which are important for the technical flow shape of the rotor.

A further development provides that the stiffening strut comprises a preferably ring-shaped hub part as well as a radial outlier. The hub part can preferably also be connected to a shaft, etc., in a shape matched manner. In addition, in particular a material agglomeration in the transition region from the hub part to the radial outlier can be prevented in order here to achieve an even higher elasticity and an avoidance of plastic deformation; in addition, elastic counter tension forces are hereby prevented with a suitable design.

The stiffening strut can generally comprise all materials which can influence a shaping or deformability in a favorable manner, preferably metals or plastics.

All embodiments of the rotor preferably have three states. That is a first state in which the rotor is free of force and the stiffening strut or the impeller blade protrudes radially. In a second state, the impeller blade is radially compressed or lies tangentially at the hub/axle.

In the third state, a deformation from the first state takes place by fluid counter-pressure or centrifugal forces. In this respect, the rotor/the stiffening strut/the impeller blade is preferably to be designed so that, considered from the first state, the deformation into the second state takes place in an opposite direction (of rotation) than on the deformation from the first state into the third state.

This is in particular useful in the aforesaid weakened embodiments of the stiffening strut since the weakening here provides that particularly small forces are required on the compression and, on the other hand, a defined working position is present here by the stiffening/the abutment in the operating state (third state) which is favorable from a technical flow aspect and serves the good design of the rotor/of a pump.

It must again be noted that all the rotors/impeller blades proposed here are in particular suitable for use in intraventricular blood pumps. These pumps have a compressed state (second state, see above) in which the rotor is introduced into a lock, for example. In this "introduction state", the blood pump is then introduced into a vessel of the body, for example into the left ventricle of a human or of an animal. The rotor is then conducted out of the lock before the pump operation so that the third state is then adopted after the start of the rotary movement. At the end of the pump operation, the repeated introduction of the rotor into the lock and the removal of the pump takes place.

BRIEF DESCRIPTION OF THE DRAWINGS

The invention will be shown and subsequently described in the following with reference to embodiments in a drawing. There are shown.

DETAILED DESCRIPTION OF THE INVENTION

Figure 1:
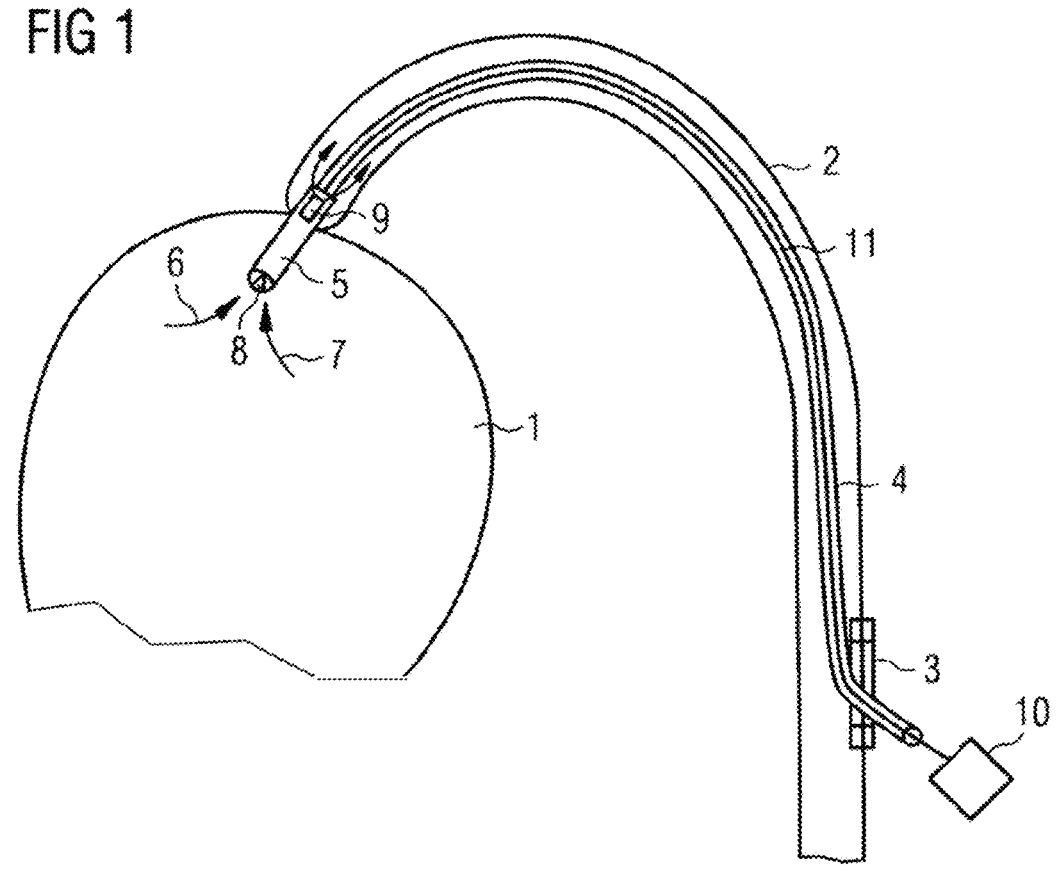
FIG. 1 schematically, a rotor blood pump which is introduced into the left ventricle of a heart by means of a hollow catheter.

FIG. 1 schematically shows the left ventricle 1 of a cardiac chamber 1 as well as a blood vessel 2 opening into it into which a hollow catheter 4 can be introduced by means of a lock 3. Said hollow catheter holds a pump 5 at its distal end and said pump projects at least partially into the ventricle 1. The pump 5 has a suction cage 8 at its distal end into which blood is sucked, as indicated by the arrows 6, 7. Said blood is pressed out by outflow openings 9 within the blood vessel 2 behind the cardiac valve. The pump 5 has a rotor having conveying elements which is rotatably drivable about its longitudinal axis by means of a flexible shaft 11 which extends through the hollow catheter 4 and is connected to a drive motor 10 outside the body of the patient. The typical speed of the rotor in operation is at some thousand up to approx. 50,000 r.p.m.

Figure 2:
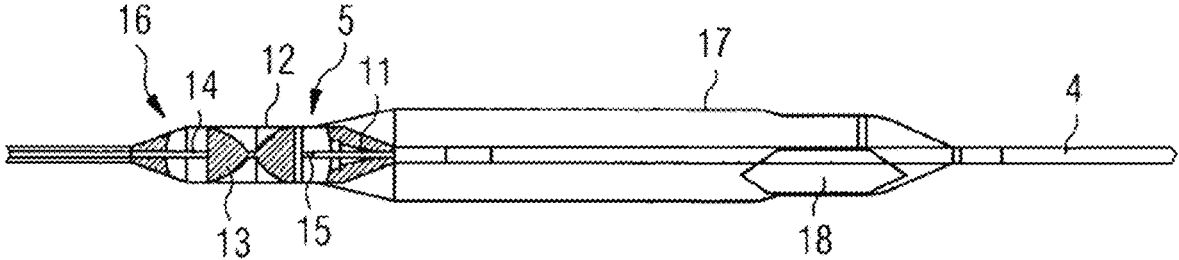
FIG. 2 the pump, in a more detailed representation.

The pump 5 having the rotor 13 is shown in more detail in FIG. 2. The rotor 13 is in each case rotatably supported within a pump housing 12 by means of a rotor shaft 14 at the proximal end 15, i.e. at the end closer to the lock 3, as well as at the distal end 16. Past the bearing at the distal end 16 or between the distal end and the rotor 13 itself, suction openings for the blood are provided, for example in the form of a suction cage, i.e. a piercing of the housing 12.

The rotor 13 itself is made in one part, having a hub and two helical impeller blades connected in one piece to said hub.

An outflow hose 17 starts at the pump housing 12 and is positioned, on a correct positioning of the pump within the cardiac valve, at the transition between the blood vessel 2 and the ventricle 1 so that the outflow openings 18 lie within the blood vessel 2. At the distal end of the pump 5, there is an additional spacer part which is bent over at the free end, for example of spiral shape, to prevent the crashing of the pump at the body tissue and moreover to facilitate the pushing of the pump through a blood vessel. In addition, the element should prevent the pump from sucking tight to vessel walls or to the inner walls of the cardiac chamber.

Figure 3:
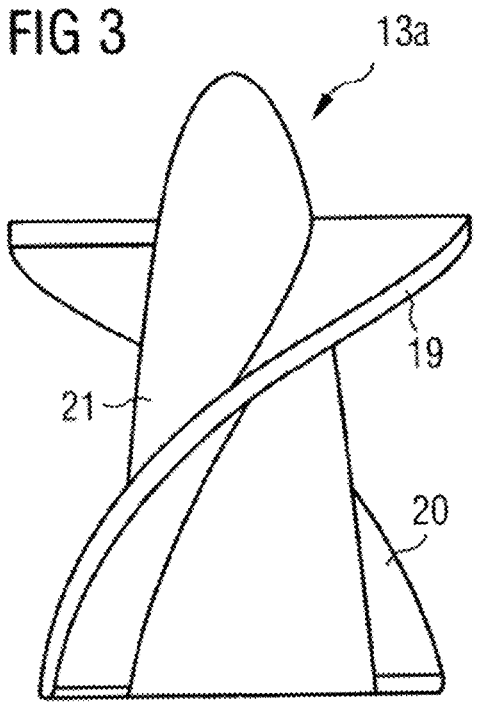
FIG. 3 schematically, an embodiment of a rotor with a hub.

FIG. 3 shows a rotor 13*a* having two helical impeller blades 19, 20 which are made from plastic, are made in one piece with the hub 21 and can, for example, receive support struts in their interior. The impeller blade body of the impeller blades 19, 20 can be made, for example, from polyurethane in solid form or from a foam and the struts can be integrated into the body. The manufacture can take place in that the struts are insert molded with a corresponding plastic.

Figure 4:
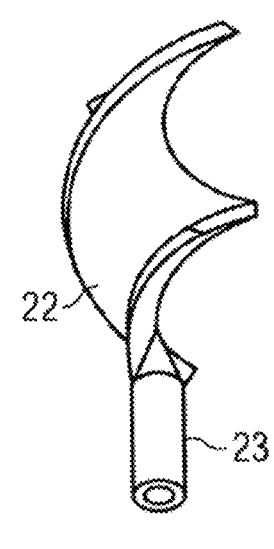
FIG. 4 an embodiment of a rotor with a hubless impeller blade.

FIG. 4 schematically shows in a three-dimensional view a rotor without a hub with a single impeller blade 22. Corresponding struts can also be embedded in it. The impeller blade 22 is driven at the end face via a shaft piece 23.

Figure 5:
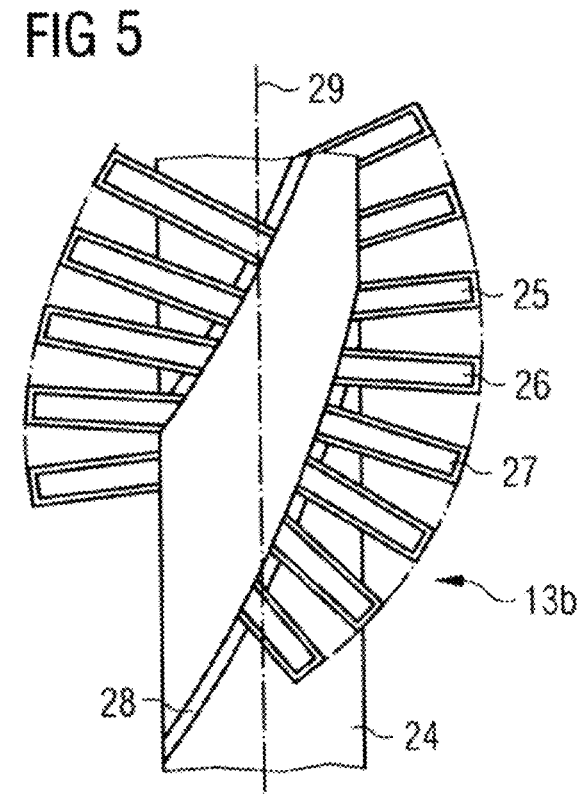
FIG. 5 the structure of a rotor with a hub and reinforcement struts for the impeller blade body.

FIG. 5 shows a rotor 13*b* having a hub 24 as well as two rows of struts 25, 26, 27 which are distributed circumferentially at the hub in the form of a helix in each case and project radially from said hub. The struts 25, 26, 27 can, for example, each comprise a pair of two individual struts which are connected to one another at their end remote from the axis of rotation. The axis of rotation is marked by 29 in FIG. 5.

Loops which can be anchored easily in an impeller blade body are formed by the struts 25, 26, 27 in this manner.

The struts can, for example, be fastened together on a respective rail per impeller blade, with the rail being flexible and being able to be drawn into a recess 28 which runs around the hub 24.

In the named example, respectively directly adjacent struts are thus connected to one another pair-wise and the pairs are connected to one another in their region close to the axis of rotation.

Figure 6:
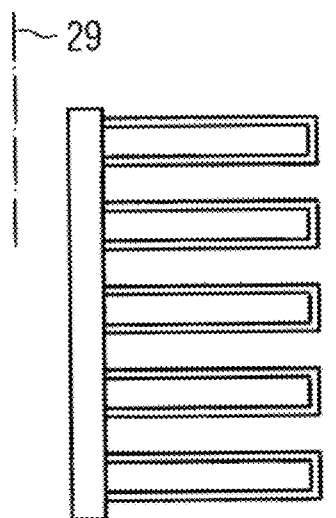
FIG. 6 a configuration of struts for a rotor, with the struts projecting perpendicularly from the longitudinal axis of the rotor.
Figure 7:
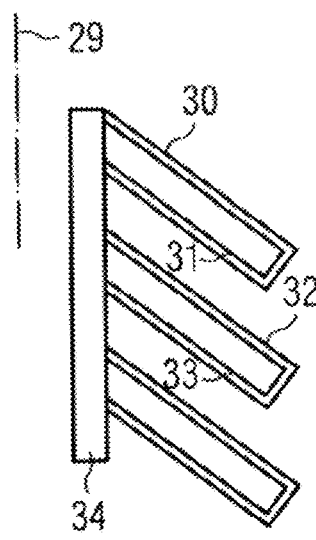
FIG. 7 a configuration with struts which are inclined with respect to the axis of rotation.

FIG. 7 shows struts 30, 31, 32, 33 which are each connected to one another pair-wise in their region remote from the axis of rotation 29 and are connected by means of a throughgoing rail 34 in the region close to the axis of rotation. The individual struts 30, 31, 32, 33 extend at an inclination with respect to the axis of rotation 29, for example at an angle of approximately 30° to 60°. In contrast to this, FIG. 6 shows struts which project radially perpendicularly from the axis of rotation 29.

Figure 8:
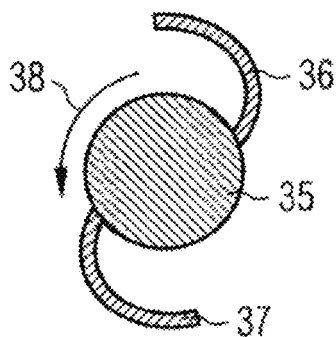
FIG. 8 a cross-section through a rotor with a solid hub.

FIG. 8 shows a cross-section through a rotor having a solid hub 35 at whose surface at the jacket side two impeller blades 36, 37 are shown located in the second state, i.e. in a slightly pre-curved form. In operation, i.e. on rotation of the rotor in the direction of the arrow 38, the impeller blades 36, 37 are erected further almost up to extension.

The rotor can also be further compressed with respect to the configuration shown in FIG. 8 in that the impeller blades are pressed more closely toward the hub 35.

Figure 9:
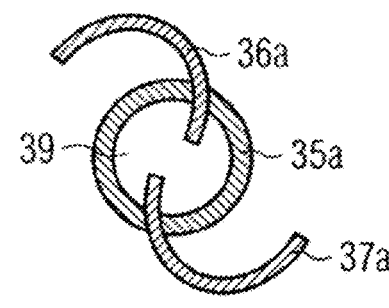
FIG. 9 a cross-section through a rotor with a hollow hub.

FIG. 9 shows two impeller blades 36*a*, 37*a* which project into a hollow space 39 of a hub 35*a*. The impeller blades 36*a*, 37*a* thereby form two-arm levers which are each supported in the wall of the hollow hub 35*a*.

Figure 10:
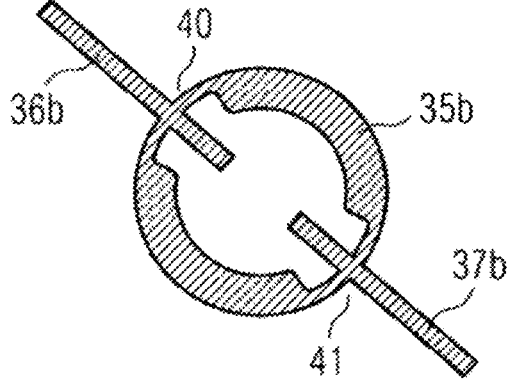
FIG. 10 a cross-section through a rotor with a hollow hub and two impeller blades which are suspended in recesses of the hub.

FIG. 10 shows a further development of the embodiment of FIG. 9 in that the wall thickness is weakened in the hub 35*b* in the region 40, 41 where the impeller blades 36*b*, 37*b* pass through the wall of the hub 35*b*. The impeller blades are thereby pivotably supported in kinds of film hinges in corresponding regions of the hub.

Figure 11:
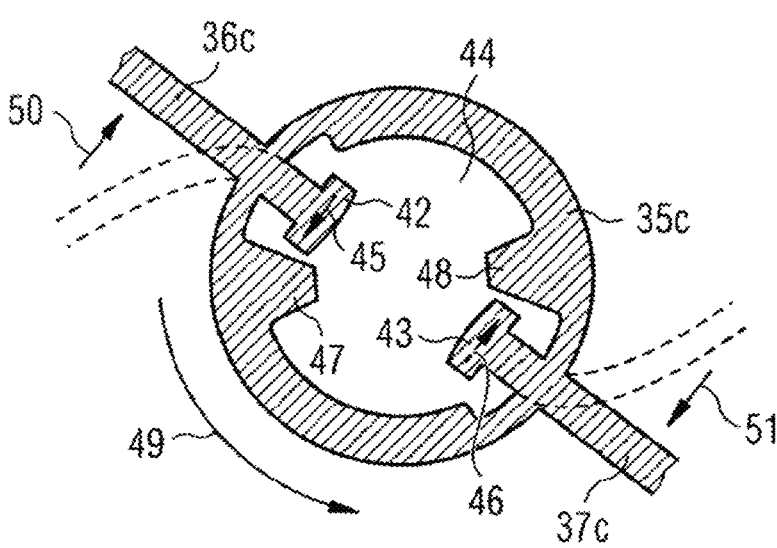
FIG. 11 a rotor in cross-section with a hollow hub and abutment bodies.

FIG. 11 shows a corresponding constellation in which inner ends and abutment bodies 42, 43 fastened thereto of the two impeller blades 36c, 37c each project into the hollow space 44 of a hub 35c. In the inner space of the hub, the abutment bodies 42, 43 cooperate in the direction of the arrows 45, 46 in the operation of the rotor with corresponding abutments 47, 48 so that the impeller blades 36c, 37c are supported in the third state and so adopt the desired operation state.

On the compression movement, the abutment bodies 42, 43 release from the abutments 47, 48 and the impeller blades 36c, 37c can be brought into the positions drawn in dashed lines in FIG. 11. In this respect, the impeller blades are pivoted within the corresponding weakened regions of the hub body 35c.

The sense of rotation of the rotor shown in operation is shown in FIG. 11 by the arrow 49, whereas the fluid counter-pressure on the impeller blades is symbolized by the arrows 50, 51.

Figure 12:
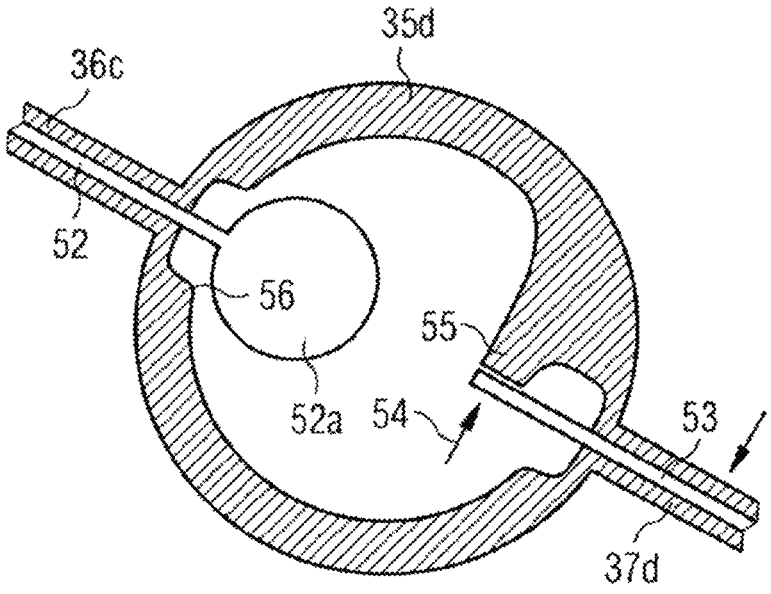
FIG. 12 a rotor in cross-section with a hollow hub and struts of two impeller blades projecting into said hollow hub with a corresponding abutment configuration.

FIG. 12 shows a further embodiment of a rotor having a hub body 35d and two impeller blades 36d, 37d which each have the struts 52, 53. In the embodiment, the impeller blades end at the outer jacket surface of the hub 35d and only the struts 52, 53 project into the interior of the hub. The strut 53 there abuts an abutment 55 in the direction of the arrow 54 in the inner space of the hub when the third state of the rotor is reached. The corresponding impeller blade 37d is thereby supported.

Another configuration is shown oppositely disposed with reference to the impeller blade 36d. The representation of different configurations of impeller blades at a rotor is only done by way of example here.

The strut 52 of the impeller blade 36d extends in the interior of the hub 35d in an abutment body 52a of the shape of a circular disc which can be made in one piece with the strut 52 and can, for example, be stamped out of a metal sheet. The abutment body 52a is shaped so that, on a corresponding load in the third state, it abuts an abutment 56 which in this case does not require any special design for limiting the movement of the impeller blade 36d.

A plurality of the abutments 52a can also be connected to one another within a rotor to form a structure for the struts 52 and to hold them while they are, for example, being insert molded with the material of the impeller blade body.

Figure 13:
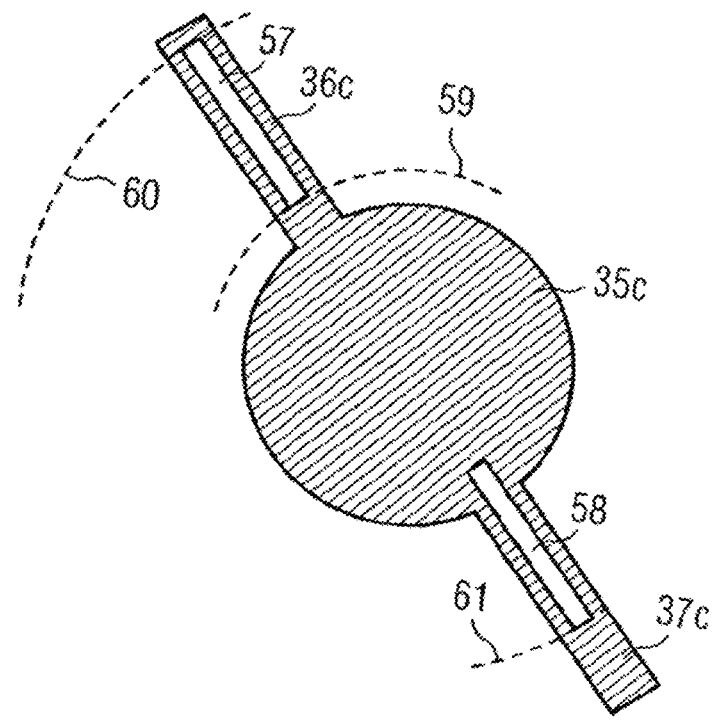
FIG. 13 in cross-section, a rotor with two impeller blades and struts embedded therein.

FIG. 13 shows a rotor having a hub 35e in a solid construction, having two impeller blades 36e, 37e into which respective struts 57, 58 are integrated. The strut 57 extends from a first axial spacing, shown by the dashed line 59, up to a second axial spacing, shown by the line 60. The strut 57 accordingly does not extend up to the hub 35c.

The strut 58 extends up to and into the hub 35e and ends at the axial spacing 61, i.e. it is radially shorter than the impeller blade 37e with respect to the rotor axis. The differences of the struts 57, 58 are only shown by way of example in a single rotor.

In the named examples, the struts are each insert molded with the material of the impeller blade body and adhere partially or at all sides to the material.

Figure 14:
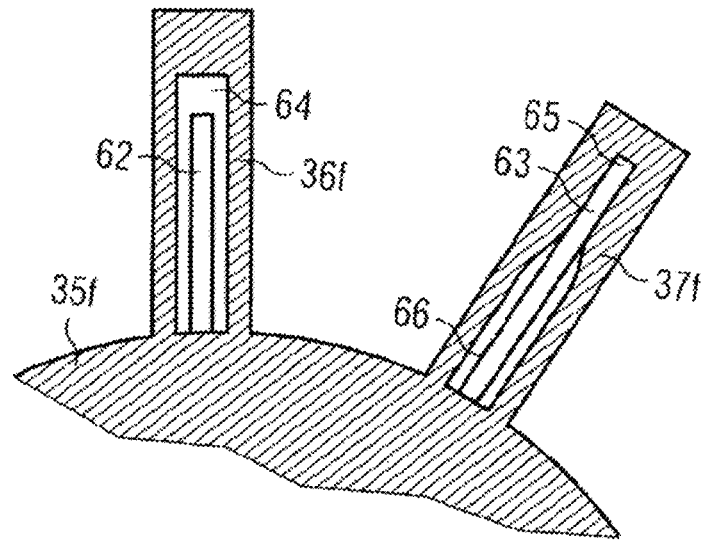
FIG. 14 in partial cross-section, a rotor with two impeller blades into which the struts are integrated within hollow spaces.

In FIG. 14, a hub 35f is shown having two exemplary impeller blades 36f, 37f which each receive a strut 62, 63. The strut 62 is smaller with respect to the length and to the width than the hollow space 64 in which it is located within the impeller blade 36f. The strut 63 is fixedly surrounded at its radially outer end 65 by the material of the impeller blade 37f and can move in the region 66 close to the axis or rotation within the hollow space of the impeller blade 37f and there adopt different positions in dependence on the state of compression or expansion, i.e. lie at different walls of the hollow space. This hollow space can be of asymmetrical design.

It is made possible by this constellation that in a position, for example, in the third state of the rotor, the corresponding strut 63 can support the impeller blade 37f, whereas the rotor can be highly compressed without a support effect of the strut in that the strut can escape within the impeller blade. Provision can correspondingly also be made that that strut is fixedly surrounded and is fixed in the impeller blade only at its end close to the axis and has movement play in the region remote from the axis.

Figure 15:
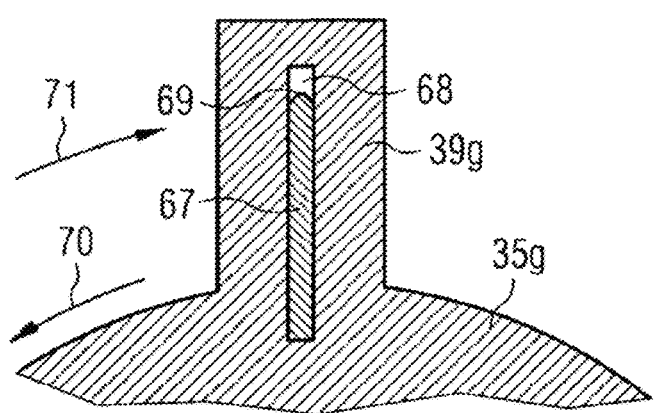
FIG. 15 in cross-section, a rotor with an impeller blade and a strut integrated therein in a hollow space which is longer than the strut.

In FIG. 15, a rotor having a hub 35g as well as an impeller blade 36g with a strut 67 integrated therein is shown. The strut 67 is made shorter in the radial direction than the hollow space 68 within the impeller blade 36g so that in operation the strut can slip, for example by centrifugal forces, radially outwardly and can there support the impeller blade. On a compression movement, for example by corresponding slopes at the radially outer end of the strut, said strut can then be displaced radially inwardly so that it impedes a compression less than in the radially outer region. The slopes are shown at the radially outer end of the strut 67 and are marked by 69. The rotary movement of the rotor is symbolized by the arrow 70 and the fluid counter-pressure against the impeller blade 36g by the arrow 71.

Figure 16:
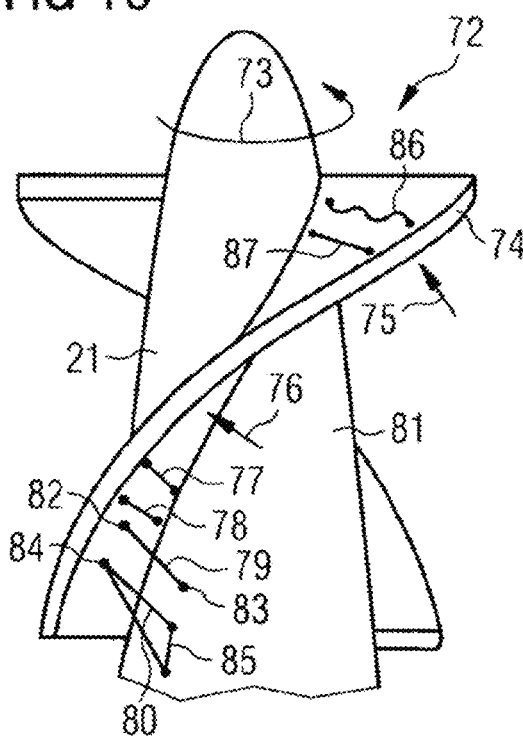
FIG. 16 a three-dimensional outside view of a rotor with impeller blades and elements with tensile strength for supporting the impeller blades.

FIG. 16 shows in a three-dimensional view a rotor 72 which rotates in the direction of the arrow 73 in operation. Forces result accordingly at the impeller blades 74 as a consequence of the fluid counter-pressure which are shown by the arrows 75, 76.

In the Figure, tensile elements 77, 78, 79, 80 are shown which represent different examples for their alignment and fastening. The tensile elements 77, 78 extend, for example, from a radially outer point at the impeller blade 74 to a radially inner point close to the hub 81. The tensile element 79 is, on the one hand, fastened to a point 82 at the impeller blade 74; on the other hand, to the point 83 on the surface of the hub 81 at a distance from the foot of the impeller blade. The tensile element 80 is formed areally as a thin film and is fastened at a point 84 to the impeller blade, whereas the base 85 is fastened on the surface of the hub 81 at a spacing from the foot of the impeller blade 74. The film 80 can be aligned such that it does not impede the fluid flow.

In the compressed second state or in the first state of the rotor, the corresponding tensile elements are slack and do not impede any movement of the impeller blades 74. In the third state, when the impeller blades are extended, the tensile elements limit a further overextension and thus stabilize the impeller blades.

The tensile elements can, for example, comprise a band having glass fiber reinforcement or can substantially comprise only glass fibers or also polycarbonate fibers, for example Kevlar, to achieve a thickness which is as low as possible with a correspondingly high tensile force and strength. The tensile elements can, however, also comprise a polymer film, for example PEEK or also a metal film, for example nitinol or titanium, to achieve the desired effect.

Basically, those materials or material combinations are particularly suitable for these flexible tensile elements which are also used for so-called non-compliant balloon catheters, since these usually combine the mechanical properties desired here with the likewise required biocompatible and blood-compatible properties.

In addition, two tensile elements 86, 87 are drawn at the impeller blade 74, with the tensile element 86 being adhered, printed on or fastened in another way on the surface of the impeller blade 74 and having a winding form which is only present in this form in the first or second states of the impeller blade. If the impeller blade is extended to the third state, this tensile element adopts the extended form marked by 87 in order then to be taut and to prevent a further movement of the impeller blade beyond the extended state.

Figure 17:
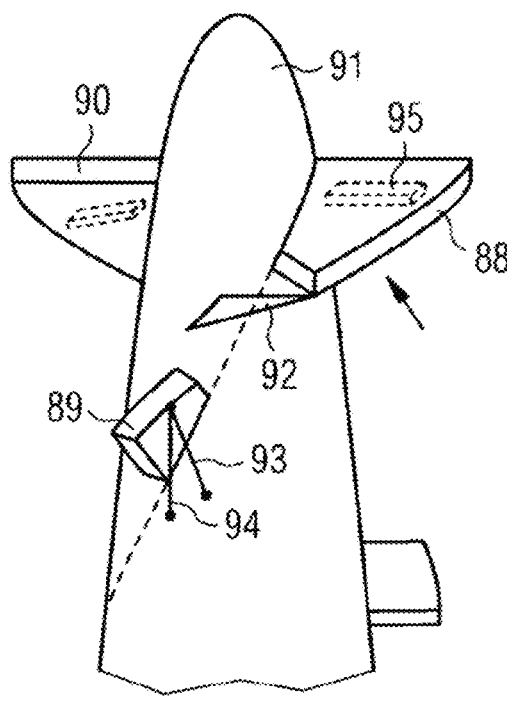
FIG. 17 a rotor with a plurality of impeller blades and various tensile elements supporting them.

In FIG. 17, a rotor having a plurality of impeller blades 88, 89, 90 is shown which each run around the hub 91 only in part and which can individually be supported by means of tensile elements 92, 93, 94. The tensile elements 92 can be formed as films and continue the contour of the corresponding impeller blades 88 in a hydrodynamically favorable manner. They are positioned and tensioned so that they support the impeller blades in the extended state. In addition, the impeller blades 88, 89, 90 can have struts 95 integrated in them.

The named variants in the embodiment of the invention represent, individually and in combination with one another, efficient measures for supporting impeller blades built as composite bodies at a rotor of a pump.

The corresponding rotors can each be arranged in a compressible and expandable housing which can be expanded, for example, by means of the erecting impeller blades.

Figure 18:
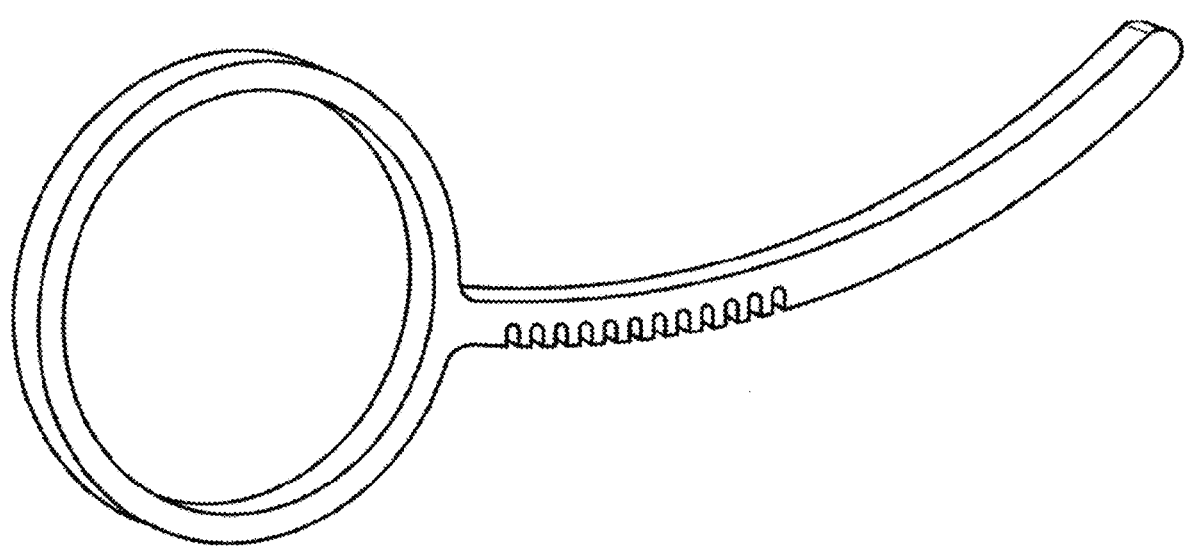
FIGS. 18 to 20 an embodiment of a reinforcement strut in different states, wherein the strut has recesses on the flow suction side for better compressibility, with the recesses being largely closed in the operating state and forming an abutment together with the embedded base material.
Figure 19:
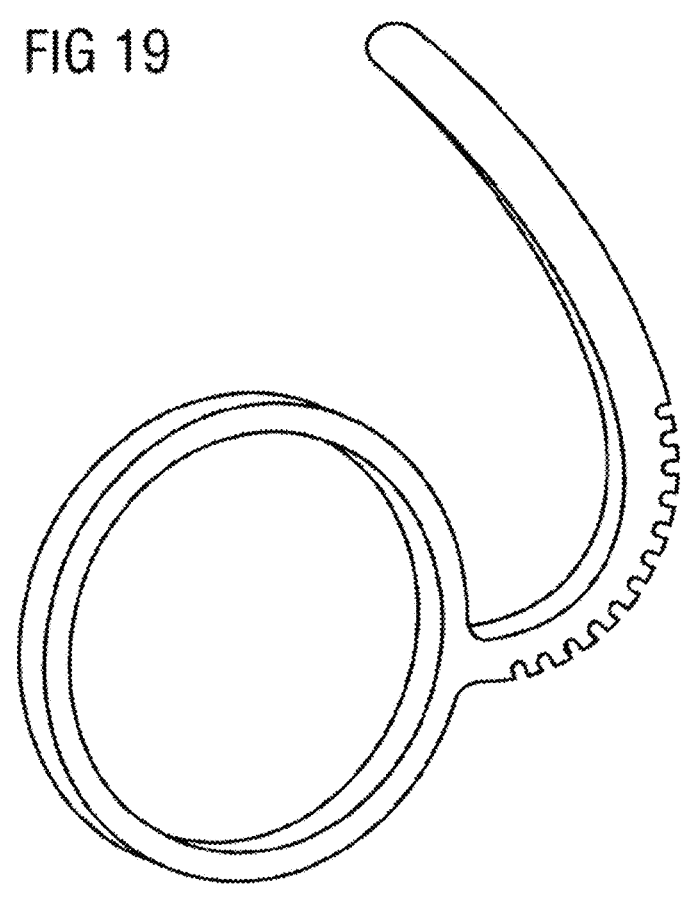
Figure 20:
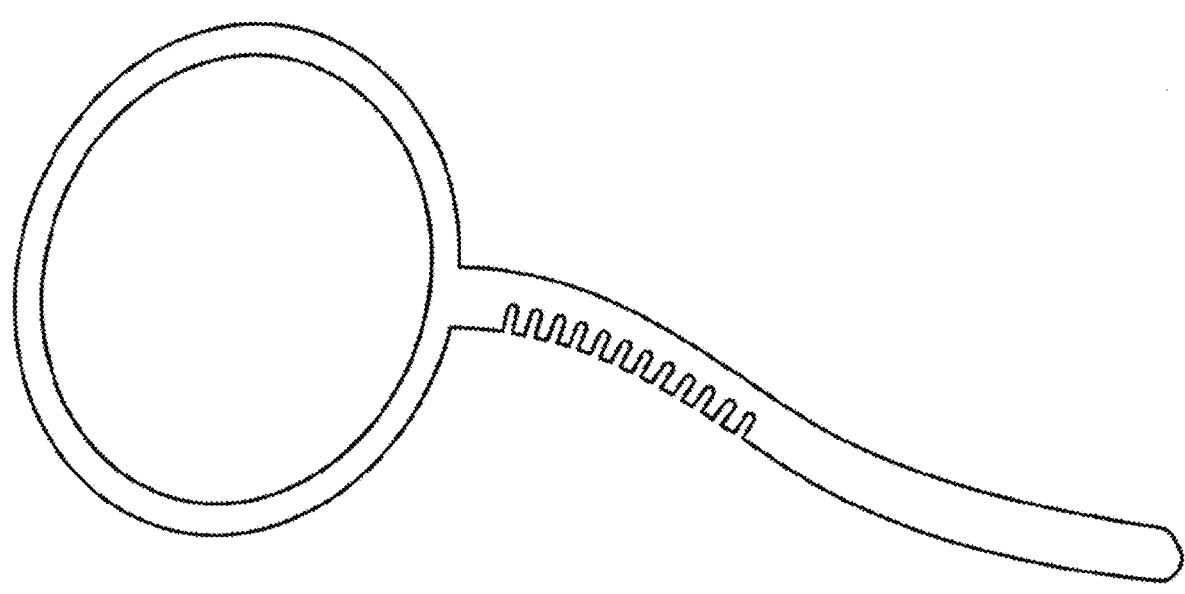

FIGS. 18 to 20 show a further embodiment of a stiffening strut. In this respect, the first state is shown in FIG. 18, that is the force-free state. In FIG. 19, the second state is shown, that is the state in which the stiffening strut/the impeller blade/the rotor is radially compressed.

This is primarily done in the present case by a tilting of the stiffening strut in FIG. 19 to the left, i.e. counter clockwise. In FIG. 20, the third state is shown, that is the operating state of the rotor/of the impeller blade/of the stiffening strut in which fluid is actually conveyed. In this respect, the fluid counter-pressure acts clockwise, i.e. the direction of rotation of the rotor is counter-clockwise. In this respect, a weakening on the flow suction side is shown (to be seen at the bottom in FIG. 20 at the radial outlier of the stiffening strut). The flow pressure side is not weakened in this case.

In FIGS. 18 to 20, only the stiffening strut is shown, without any additional material in which the stiffening strut is embedded. In the present case, this stiffening strut is attached to the axial front flow edge of the rotor and the radial outlier of the stiffening strut projecting to the right in FIG. 8 is completely surrounded by the embedding material, plastic in the present case. This is also the case between the weakening slits. The impeller blade surface is in this respect of a property such that no weakening is visible from the outside. It must additionally be noted that the compression (see FIG. 19) is particularly simple, whereas a "mechanical abutment" is present in the state shown in FIG. 20. In this respect, the inner walls of the slits do not have to abut one another since the embedding compound/embedding material/plastic located in this intermediate region is compressed and thus a deformation limitation is guaranteed.

Figure 21:
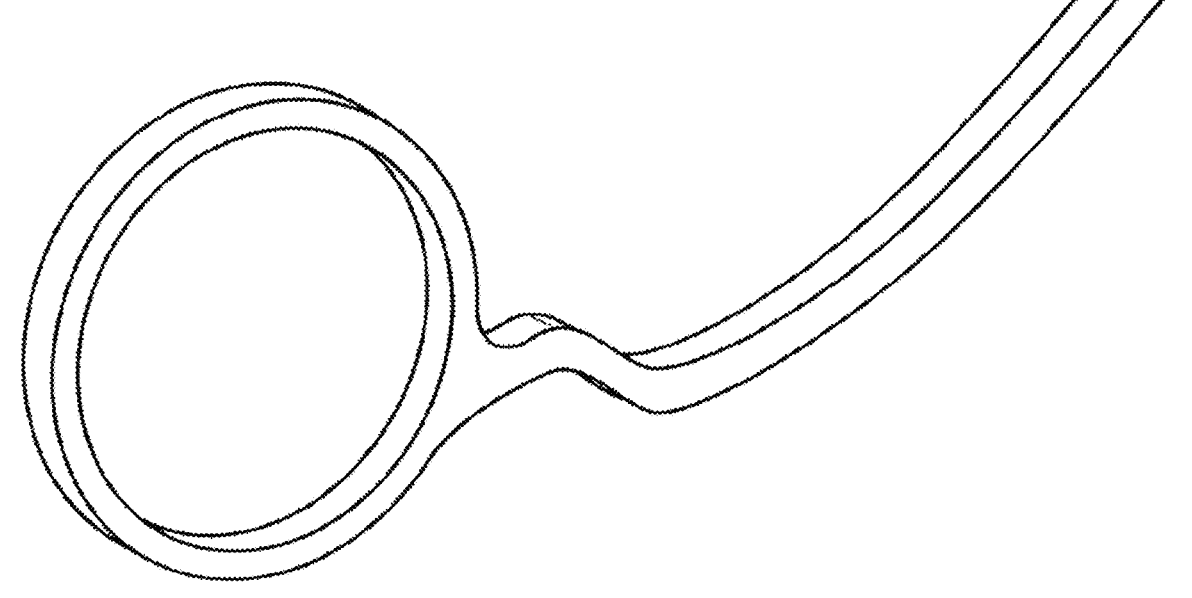
FIGS. 21 to 23 an embodiment of a reinforcement strut in different states, with the strut being optimized with respect to uniform stress distributions in the material.
Figure 22:
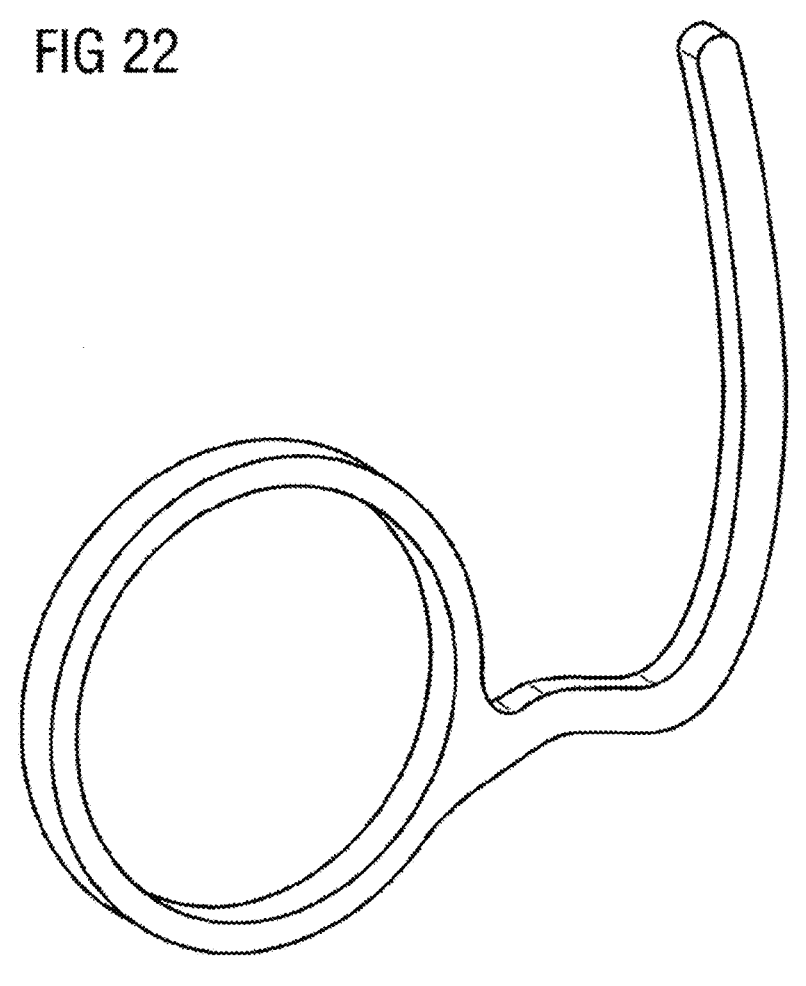
Figure 23:
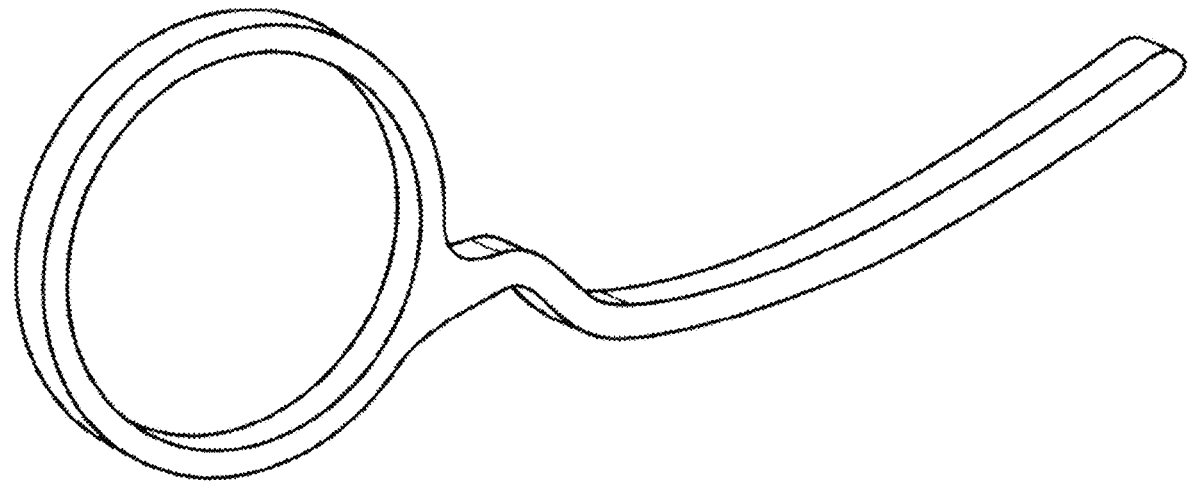

FIG. 21 in turn shows the first state in which the deformation strut/the rotor projects in a force-free manner. All the features are formed as in the aforesaid embodiment in accordance with FIGS. 18-20, provided that nothing is otherwise stated in the following. In the embodiments in accordance with FIGS. 21-23 (FIG. 22 shows the second state; FIG. 23 in turn the third state), no weakening in the form of slits is shown; instead a kink is shown close to the circular hub region which shows a "reinforcement curvature". This is designed so that, on the one hand, on the elastic deformation into the state shown in FIG. 22, a slight bending over is possible and, on the other hand, in the state in accordance with FIG. 23, a mechanical abutment is present without the plastic region of the material ever being entered, on which irreversible deformations would occur.

Figure 24:
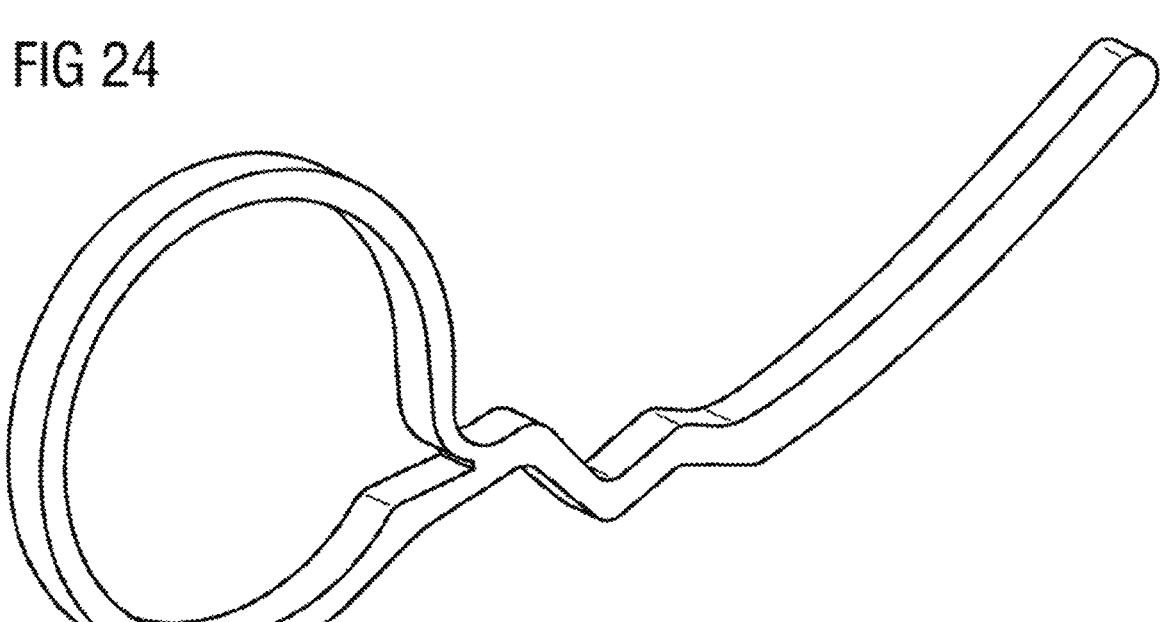
FIGS. 24 to 26 an embodiment of a reinforcement strut in different states, with the strut and a flexible tensile element being formed in one part.
Figure 25:
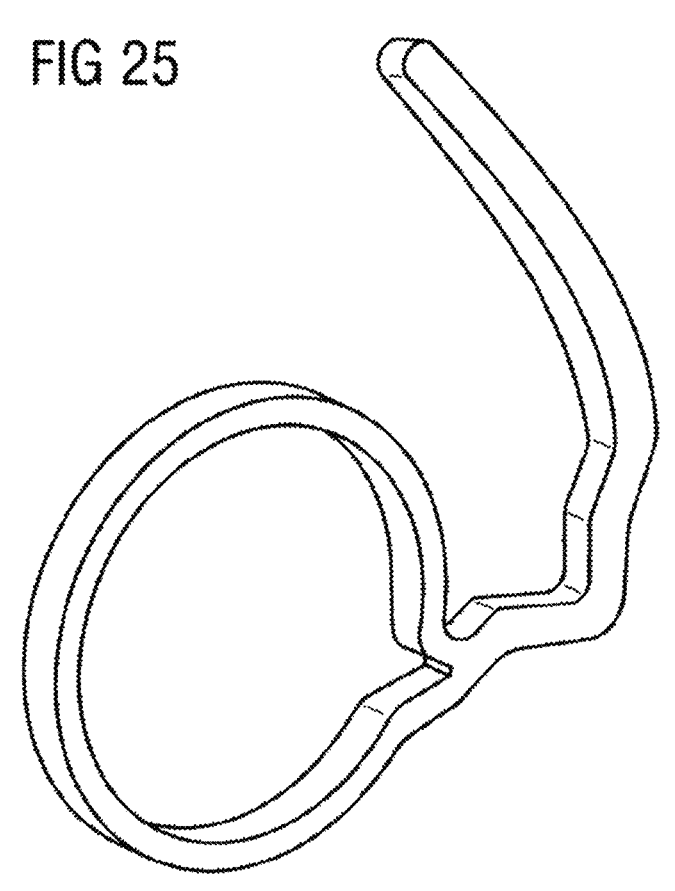
Figure 26:
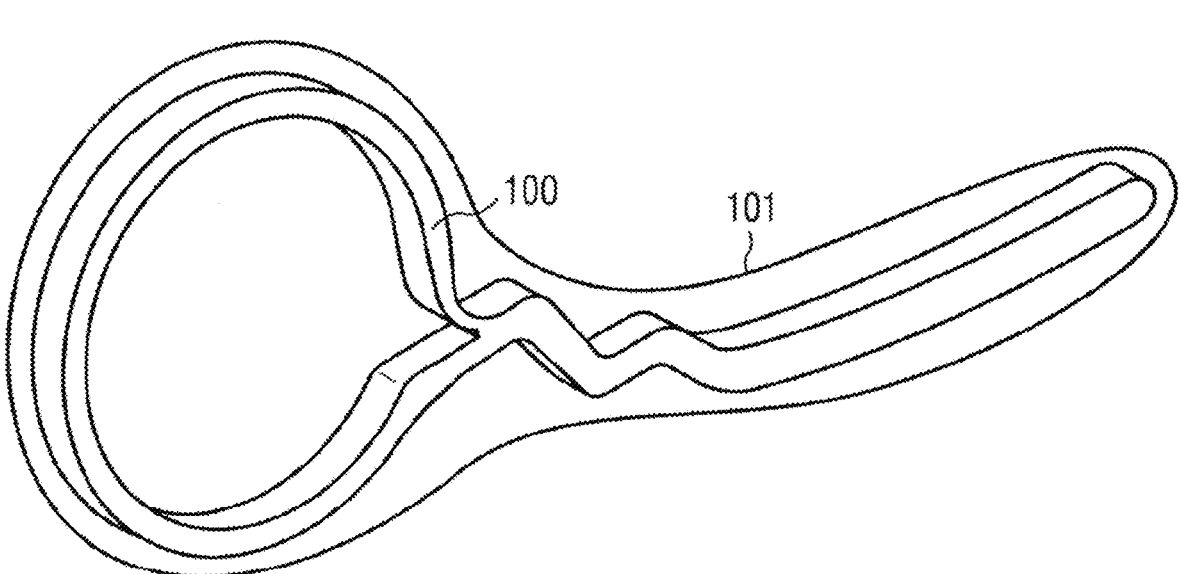

FIGS. 24 to 26 show a further embodiment which is similar to the embodiment in accordance with FIGS. 21-23, with, however, a radially inwardly weakening located in the hub ring being shown in the transition region from the annular hub region toward the radial outlier, said weakening facilitating the elasticity of the outlier above all on the movement from the first state shown in FIG. 24 to the second state shown in FIG. 25. In addition, the ensuring of the mechanical abutment in the third state shown in FIG. 26 is also ensured by a suitable configuration, said third state being able to take place, for example, by the design of the tapered region (100) as a tensile strut. The tapered region (100) is thereby easily bendable on the adoption of the first state, but adopts in the third state an approximately extended form which sets an increased resistance toward deflection under the flow pressure.

It must again be mentioned that it is in each case assumed in FIGS. 20, 23 and 26 that the direction of rotation of the rotor is counter clockwise and that thereby an expansion of the radial outlier in the clockwise direction results. The outline of an impeller blade 101 is furthermore schematically shown in FIG. 26 which completely surrounds the strut in the embodiment shown such that the fluid comes into contact with a homogeneous surface which is as uniform as possible. This ensures that the fluid undergoes an acceleration in the operating state which is as smooth as possible with small shear tension peaks.

The invention claimed is:

1. A radially compressible and expandable rotor for a pump, the rotor comprising:
   at least one impeller comprising an impeller blade, wherein the impeller blade has an impeller blade body made of material that is elastically deformable; and
   at least one stiffening strut configured to stiffen the impeller blade, wherein the at least one stiffening strut includes at least one weakening configured to provide a holding force to limit deformation of the impeller blade,
   wherein the at least one weakening is a plurality of slits disposed in a longitudinal direction along the at least one stiffening strut.

2. The rotor of claim 1, wherein the at least one stiffening strut is at least partially embedded in the material of the impeller blade body.

3. The rotor of claim 1, wherein the at least one stiffening strut is completely embedded in the material of the impeller blade body.

4. The rotor of claim 1, wherein the impeller blade is configured to rotate about a hub to convey a fluid.

5. The rotor of claim 4, wherein the fluid is blood.

6. The rotor of claim 4, wherein the impeller blade includes first and second sides oriented such that, when the impeller blade rotates about the hub, the first side is a suction side and the second side is a pressure side.

7. The rotor of claim 4, wherein a thickness of the impeller blade body in a direction between a pressure side and a suction side amounts to at least 80% of a thickness of the at least one stiffening strut in the same direction.

8. The rotor of claim 4, wherein a thickness of the impeller blade body in a direction between a pressure side and a suction side amounts to at least 100% of a thickness of the at least one stiffening strut in the same direction.

9. The rotor of claim 4, wherein a thickness of the impeller blade body in a direction between a pressure side and a suction side is greater than a thickness of the at least one stiffening strut in the same direction.

10. The rotor of claim 1, wherein the impeller blade is configured to be radially compressed from a first deployed state to a second compressed state.

11. The rotor of claim 10, wherein the impeller blade is configured to expand beyond the first deployed state to a third operational state.

12. The rotor of claim 11, wherein the impeller blade is configured to assume the third operational state under fluid counter pressure.

13. The rotor of claim 11, wherein the impeller blade is configured to assume the third operational state due to centrifugal forces that occur during rotation of the impeller blade about a hub.

14. The rotor of claim 1, wherein the at least one stiffening strut is insert molded with the material of the impeller blade body.

15. The rotor of claim 1, wherein the material of the impeller blade body that is elastically deformable is a first material and the at least one stiffening strut is a second material.

16. The rotor of claim 15, wherein the first material is different from the second material.

17. The rotor of claim 15, wherein the second material is an elastic polymer, a memory alloy, or nitinol.

18. The rotor of claim 15, wherein the first material is plastic.

\* \* \* \* \*